(12) United States Patent
Schmidt et al.

(10) Patent No.: US 10,707,063 B2
(45) Date of Patent: Jul. 7, 2020

(54) SYSTEMS AND METHODS FOR CALIBRATION, VERIFICATION, AND SENSITIVITY CHECKS FOR DETECTORS

(71) Applicant: Rapiscan Systems, Inc., Torrance, CA (US)

(72) Inventors: Hartwig Schmidt, Tewksbury, MA (US); Michael E. Patterson, Amesbury, MA (US); Stefan R. Lukow, Hampstead, NH (US); Kenneth R. Gonthier, Amesbury, MA (US); Hanh T. Lai, Arlington, MA (US); Vibha Mishra, Andover, MA (US)

(73) Assignee: Rapiscan Systems, Inc., Torrance, CA (US)

( * ) Notice: Subject to any disclaimer, the term of this patent is extended or adjusted under 35 U.S.C. 154(b) by 0 days.

(21) Appl. No.: 15/388,589

(22) Filed: Dec. 22, 2016

(65) Prior Publication Data

US 2018/0182603 A1   Jun. 28, 2018

(51) Int. Cl.
| | |
|---|---|
| *H01J 49/14* | (2006.01) |
| *H01J 49/00* | (2006.01) |
| *G01N 27/62* | (2006.01) |
| *H01J 49/02* | (2006.01) |

(52) U.S. Cl.
CPC ........ *H01J 49/0009* (2013.01); *G01N 27/622* (2013.01); *H01J 49/025* (2013.01)

(58) Field of Classification Search
CPC .. H04N 5/33; G01J 5/522; G01T 1/40; G01D 18/00; A61B 6/583
See application file for complete search history.

(56) References Cited

U.S. PATENT DOCUMENTS

| | | |
|---|---|---|
| 5,491,337 A | 2/1996 | Jenkins |
| 5,944,048 A | 8/1999 | Bump |
| 6,211,516 B1 | 4/2001 | Syage |
| 6,326,615 B1 | 12/2001 | Syage |

(Continued)

FOREIGN PATENT DOCUMENTS

| | | |
|---|---|---|
| AT | 303589 T | 9/2005 |
| AT | 480769 T | 9/2010 |

(Continued)

OTHER PUBLICATIONS

International Search Report for PCT/US17/67632, dated Mar. 16, 2018.

*Primary Examiner* — David P Porta
*Assistant Examiner* — Mamadou Faye
(74) *Attorney, Agent, or Firm* — Novel IP (57) ABSTRACT

The present disclosure is directed to methods and systems for calibration, calibration verification, and sensitivity checks for a detector. The methods and systems include calibrating a detector by releasing at least one calibrant from at least one calibrant chamber in flow communication with the detector. The systems and methods further include verifying the calibration by releasing at least one verification substance from at least one verification chamber in flow communication with the detector. The systems and methods further include checking a sensitivity of the detector by releasing at least one sensitivity substance from at least one sensitivity chamber in flow communication with the detector.

11 Claims, 6 Drawing Sheets

(56) References Cited

U.S. PATENT DOCUMENTS

| | | |
|---|---|---|
| 6,329,653 B1 | 12/2001 | Syage |
| 6,495,824 B1 | 12/2002 | Atkinson |
| 6,630,664 B1 | 10/2003 | Syage |
| 6,642,513 B1 | 11/2003 | Jenkins |
| 6,690,005 B2 | 2/2004 | Jenkins |
| 6,708,572 B2 | 3/2004 | Jenkins |
| 6,737,642 B2 | 5/2004 | Syage |
| 6,765,198 B2 | 7/2004 | Jenkins |
| 6,815,670 B2 | 11/2004 | Jenkins |
| 6,831,273 B2 | 12/2004 | Jenkins |
| 6,840,122 B1 | 1/2005 | Jenkins |
| 7,047,829 B2 | 5/2006 | Napoli |
| 7,109,476 B2 | 9/2006 | Hanold |
| 7,119,342 B2 | 10/2006 | Syage |
| 7,141,786 B2 | 11/2006 | McGann |
| 7,161,144 B2 | 1/2007 | Syage |
| 7,196,325 B2 | 3/2007 | Syage |
| 7,253,727 B2 | 8/2007 | Jenkins |
| 7,299,710 B2 | 11/2007 | Syage |
| 7,338,638 B2 | 3/2008 | McGann |
| 7,401,498 B2 | 7/2008 | Syage |
| 7,448,248 B2 | 11/2008 | Carey |
| 7,456,393 B2 | 11/2008 | Napoli |
| 7,528,367 B2 | 5/2009 | Haigh |
| 7,541,577 B2 | 6/2009 | Davenport |
| 7,594,422 B2 | 9/2009 | Perry |
| 7,594,447 B2 | 9/2009 | Napoli |
| 7,663,099 B2 | 2/2010 | Reda |
| 7,709,788 B2 | 5/2010 | Geraghty et al. |
| 7,721,588 B2 | 5/2010 | Perry |
| 7,856,898 B2 | 12/2010 | Carey |
| 7,880,137 B2 | 2/2011 | McGann |
| 8,161,830 B2 | 4/2012 | Boudries |
| 8,186,234 B2 | 5/2012 | Syage |
| 8,288,735 B2 | 10/2012 | Syage |
| 8,402,842 B2 | 3/2013 | Syage |
| 8,434,375 B1 | 5/2013 | Syage |
| 8,614,582 B2 | 12/2013 | Syage |
| 8,686,355 B2 | 4/2014 | Patterson |
| 8,723,111 B2 | 5/2014 | Syage |
| 8,857,278 B2 | 10/2014 | Syage |
| 8,866,073 B2 | 10/2014 | Goedecke |
| 8,952,327 B2 | 2/2015 | Patterson |
| 9,147,565 B1 | 9/2015 | Goedecke |
| 9,354,153 B2 | 5/2016 | Syage |
| 9,482,655 B2 | 11/2016 | Vilkov |
| 9,528,969 B2 | 12/2016 | Shaw |
| 9,558,924 B2 | 1/2017 | Syage |
| 9,683,981 B1 | 6/2017 | Vilkov |
| 9,689,857 B1 | 6/2017 | Vilkov |
| 9,726,655 B2 | 8/2017 | Syage |
| 9,766,218 B2 | 9/2017 | Lai |
| 9,789,434 B1 | 10/2017 | Lai |
| 2005/0229716 A1 | 10/2005 | Unsworth |
| 2007/0029477 A1 | 2/2007 | Miller |
| 2007/0131017 A1* | 6/2007 | Carey ............... G01N 27/622 73/1.01 |
| 2008/0029697 A1 | 2/2008 | Willis |
| 2009/0078862 A1* | 3/2009 | Rodier ............... G01N 27/622 250/282 |
| 2009/0166524 A1 | 7/2009 | Geraghty et al. |
| 2015/0129760 A1* | 5/2015 | Beil ............... G01N 27/622 250/282 |
| 2015/0219554 A1* | 8/2015 | Hedges ............... G01N 21/39 244/135 R |
| 2016/0282304 A1 | 9/2016 | Vilkov |
| 2016/0314953 A1* | 10/2016 | Addleman ......... H01J 49/0409 |
| 2017/0103880 A1 | 4/2017 | Syage |
| 2017/0213715 A1 | 7/2017 | Davila |
| 2017/0241950 A1* | 8/2017 | McIntyre ............ G01N 27/622 |
| 2017/0261483 A1 | 9/2017 | Vilkov |
| 2017/0261484 A1 | 9/2017 | Vilkov |
| 2017/0284977 A1 | 10/2017 | Rogers |
| 2017/0309463 A1 | 10/2017 | Vilkov |
| 2018/0158665 A1 | 6/2018 | Eiceman |
| 2018/0164189 A1 | 6/2018 | Bilodeau |
| 2018/0172635 A1 | 6/2018 | Lai |
| 2018/0172650 A1 | 6/2018 | Platow |
| 2018/0182603 A1 | 6/2018 | Schmidt |
| 2018/0182604 A1 | 6/2018 | Lai |
| 2018/0283993 A1 | 10/2018 | Shaw |
| 2018/0284081 A1 | 10/2018 | Shaw |

FOREIGN PATENT DOCUMENTS

| | | |
|---|---|---|
| CA | 2153371 C | 3/1999 |
| CA | 2436256 C | 6/2007 |
| CA | 2382823 C | 11/2007 |
| CA | 2362449 C | 10/2008 |
| CA | 2411532 C | 4/2010 |
| CA | 2285153 C | 5/2010 |
| CA | 2479875 C | 2/2011 |
| CA | 2538709 C | 2/2013 |
| CA | 2790430 A1 | 3/2013 |
| CA | 2807894 A1 | 9/2013 |
| CA | 2620405 C | 7/2014 |
| CA | 2548177 C | 9/2014 |
| CA | 2844222 A1 | 9/2014 |
| CA | 2845959 A1 | 9/2014 |
| CA | 2688352 C | 6/2015 |
| CA | 2644937 C | 11/2015 |
| CA | 2904479 A1 | 3/2016 |
| CA | 2910780 A1 | 4/2016 |
| CA | 2913931 A1 | 6/2016 |
| CA | 2915785 A1 | 6/2016 |
| CA | 2924580 A1 | 9/2016 |
| CA | 2647651 C | 11/2016 |
| CA | 2738053 C | 5/2017 |
| CA | 2959791 A1 | 9/2017 |
| CA | 2959796 A1 | 9/2017 |
| CA | 2962154 A1 | 9/2017 |
| CA | 2964147 A1 | 10/2017 |
| CN | 100445767 C | 12/2008 |
| CN | 103308590 A | 9/2013 |
| CN | 105738461 A | 7/2016 |
| CN | 107037114 A | 8/2017 |
| CN | 107167334 A | 9/2017 |
| CN | 107167335 A | 9/2017 |
| CN | 107271254 A | 10/2017 |
| DE | 69528418 T2 | 1/2003 |
| DE | 69926965 T2 | 6/2006 |
| EP | 2368102 A2 | 9/2011 |
| EP | 2637013 A2 | 9/2013 |
| EP | 2778650 A2 | 9/2014 |
| EP | 2778669 A1 | 9/2014 |
| EP | 2835634 A1 | 2/2015 |
| EP | 2884254 A1 | 6/2015 |
| EP | 3015858 A1 | 5/2016 |
| EP | 3032570 A2 | 6/2016 |
| EP | 3040717 A1 | 7/2016 |
| EP | 1938078 B1 | 3/2017 |
| EP | 1297554 B1 | 4/2017 |
| EP | 3182111 A1 | 6/2017 |
| ES | 2183855 | 4/2003 |
| FR | 692712 A | 11/1930 |
| GB | 992782 A | 5/1965 |
| GB | 2075578 A | 11/1981 |
| GB | 2496286 A | 5/2013 |
| GB | 2536076 A | 9/2016 |
| JP | 3045655 B2 | 5/2000 |
| WO | 2010042881 A1 | 4/2010 |

* cited by examiner

SYSTEMS AND METHODS FOR CALIBRATION, VERIFICATION, AND SENSITIVITY CHECKS FOR DETECTORS

BACKGROUND OF THE DISCLOSURE

The embodiments described herein relate generally to detector calibration, and, more particularly, to calibration, calibration verification, and sensitivity checks for a detector. More specifically, the methods and systems include calibrating a detector by releasing a calibrant from a calibrant chamber in flow communication with the detector. The systems and methods further include verifying the calibration by releasing a verification substance from a verification chamber in flow communication with the detector. The systems and methods further include checking a sensitivity of the detector by releasing a sensitivity substance from a sensitivity chamber in flow communication with the detector.

Mobility spectrometers measure the intensity of ions arriving at a detector as a function of their drift time in order to characterize a sample. Because this drift time is dependent on experimental conditions, such as temperature and pressure, a drift time axis of the detector needs to be calibrated prior to sample analysis. When a detector is calibrated, absolute drift times are converted into "calibrated units," such that peak positions of detected ions are compared to a library entry. Verification of the calibration may be performed by introducing a sample including a known verification substance into the detector, and confirming that the calibrated units enable accurate characterization of the known verification substance. In addition, a sensitivity check to verify that the detector is configured to detect a minimum amount of a substance may be performed. The sensitivity check may be performed by introducing a sample including a known amount of a known sensitivity substance into the detector, and confirming that the detector detects the known sensitivity substance.

In at least some known systems, calibration of the detector is performed using external calibrant traps, wherein the calibrant is introduced into the detector through a desorber. These calibration traps, however, have limited lifetimes, can get contaminated, and can be costly to replace and/or refill. Moreover, these calibration processes with external traps are labor-intensive and are not easily automated. Likewise, verification of the calibration and the sensitivity checks may be performed using external traps containing the verification and sensitivity substances, respectively. These external traps face the same drawbacks described above.

Accordingly, having a system that solves and/or eliminates these issues would be desirable.

BRIEF DESCRIPTION OF THE DISCLOSURE

In some embodiments of the present disclosure, a method for internal calibration and verification of a detector is disclosed. The method includes calibrating the detector, wherein the calibration includes releasing at least one calibrant from at least one calibrant chamber in flow communication with the detector, and verifying the calibration, wherein the verification includes releasing at least one verification substance from at least one verification chamber in flow communication with the detector.

In another embodiment of the present disclosure, a method for internal calibration, verification, and sensitivity checking of a detector is disclosed. The method includes calibrating the detector, wherein the calibration includes releasing at least one calibrant from at least one calibrant chamber in flow communication with the detector, verifying the calibration, wherein the verification includes releasing at least one verification substance from at least one verification chamber in flow communication with the detector, and checking the sensitivity of the detector, wherein the sensitivity checking includes releasing at least one sensitivity substance from at least one sensitivity chamber in flow communication with the detector.

In yet another embodiment of the present disclosure, a method for internal calibration and sensitivity checking of a detector is disclosed. The method includes calibrating the detector, wherein the calibration includes releasing at least one calibrant from at least one calibrant chamber in flow communication with the detector, and checking the sensitivity of the detector, wherein the sensitivity checking includes releasing at least one sensitivity substance from at least one sensitivity chamber in flow communication with the detector.

In another embodiment of the present disclosure, a method for external calibration, internal verification, and internal sensitivity checking of a detector is disclosed. The method includes calibrating the detector, verifying the calibration, and checking the sensitivity of the detector. The verification includes releasing at least one verification substance from at least one verification chamber in flow communication with the detector, and the sensitivity checking includes releasing at least one sensitivity substance from at least one sensitivity chamber in flow communication with the detector.

In still another embodiment of the present disclosure, a system for internal calibration and verification of a detector is disclosed. The system includes at least one detector including at least one detector inlet, at least one calibrant chamber coupled in flow communication with the at least one detector inlet, and at least one verification chamber coupled in flow communication with the at least one detector inlet. The at least one calibrant chamber includes at least one calibrant and at least one calibrant control valve configured to release an amount of the at least one calibrant into the at least one detector inlet. The at least one verification chamber includes at least one verification substance and at least one verification control valve configured to release an amount of the at least one verification substance into the at least one detector inlet and verify the calibration of the at least one detector.

In another embodiment of the present disclosure, a system for internal calibration, verification, and sensitivity checking of a detector is disclosed. The system includes at least one detector including at least one detector inlet, at least one calibrant chamber coupled in flow communication with the at least one detector inlet, at least one verification chamber coupled in flow communication with the at least one detector inlet, and at least one sensitivity chamber coupled in flow communication with the at least one detector inlet. The at least one calibrant chamber includes at least one calibrant and at least one calibrant control valve configured to release an amount of the at least one calibrant into the at least one detector inlet. The at least one verification chamber includes at least one verification substance and at least one verification control valve configured to release an amount of the at least one verification substance into the at least one detector inlet and verify the calibration of the at least one detector. The at least one sensitivity chamber includes at least one sensitivity substance and at least one sensitivity control valve configured to release an amount of the at least one sensitivity substance into the at least one detector inlet and analyze the sensitivity of the at least one detector.

In yet another embodiment of the present disclosure, a system for internal calibration and sensitivity checking of a detector is disclosed. The system includes at least one detector including at least one detector inlet, at least one calibrant chamber coupled in flow communication with the at least one detector inlet, and at least one sensitivity chamber coupled in flow communication with the at least one detector inlet. The at least one calibrant chamber includes at least one calibrant and at least one calibrant control valve configured to release an amount of the at least one calibrant into the at least one detector inlet. The at least one sensitivity chamber includes at least one sensitivity substance and at least one sensitivity control valve configured to release an amount of the at least one sensitivity substance into the at least one detector inlet and analyze the sensitivity of the at least one detector.

In a further embodiment of the present disclosure, a system for external calibration, internal verification, and internal sensitivity checking of a detector is disclosed. The system includes at least one detector including at least one detector inlet, at least one calibration component configured to calibrate the at least one detector, at least one verification chamber coupled in flow communication with the at least one detector inlet, and at least one sensitivity chamber coupled in flow communication with the at least one detector inlet. The at least one verification chamber includes at least one verification substance and at least one verification control valve configured to release an amount of the at least one verification substance into the at least one detector inlet and verify the calibration of the at least one detector. The at least one sensitivity chamber includes at least one sensitivity substance and at least one sensitivity control valve configured to release an amount of the at least one sensitivity substance into the at least one detector inlet and analyze the sensitivity of the at least one detector.

DETAILED DESCRIPTION OF THE DISCLOSURE

The embodiments disclosed herein improve calibration of detectors, verification of the calibration, and checking the sensitivity of the detectors. More specifically, the embodiments disclosed herein provide calibration, verification, and sensitivity check chambers that enable automated calibration, verification, and sensitivity checks. When providing these chambers internally, these processes are less labor-intensive and require smaller sample sizes of the calibration, verification, and sensitivity substances, which, in turn, reduces the cost of these systems in comparison to systems employing external traps. In addition, introducing any substance other than a sample (e.g., including a substance of interest) may constitute a possibility for charge competition between the substance and the sample and/or overlapping peaks in a detected signal that may compromise the response by either reducing the intensity of the target peak or altering its peak position. Using the calibration, verification, and sensitivity check chambers provided herein enables corresponding calibration, verification, and sensitivity checks to be performed quickly, thereby reducing the time any non-substance sample is introduced into the detector. Moreover, in some embodiments, these processes are performed at regular intervals, further reducing the amount of substance needed as well as the processing time.

The present disclosure is directed to calibrating a detector (either internally or externally), verifying the calibration of the detector, and checking the sensitivity of the detector. In particular, a detection system includes an internal calibrant chamber containing a calibrant. The calibrant is introduced into the detector for detection of the calibrant and calibration of the detector. In some embodiments, the detection system further includes an internal verification chamber containing a verification substance. The verification substance is introduced into the detector for detection of the verification substance and verification of the calibration of the detector. In some embodiments, the detection system also includes an internal sensitivity chamber containing a sensitivity substance. The sensitivity substance is introduced into the detector for detection of the sensitivity substance and to check the sensitivity of the detector.

In some embodiments, the detector of the present disclosure (also referred to herein as an "analysis device") includes at least one of an ion mobility spectrometer (IMS), an ion trap mobility spectrometer (ITMS), a drift spectrometer (DS), a non-linear drift spectrometer, a field ion spectrometer (FIS), a radio frequency ion mobility increment spectrometer (IMIS), a field asymmetric ion mobility spectrometer (FAIMS), an ultra-high-field FAIMS, a differential ion mobility spectrometer (DIMS) and a differential mobility spectrometer (DMS), a traveling wave ion mobility spectrometer, a mass spectrometer (MS), a gas chromatograph (GC), and combinations thereof.

In some embodiments, the method includes using an ionization source to ionize one or more substances (e.g., a sample, calibrant, verification substance, and/or sensitivity substance) within the detector. The ionization source is any ionization system that enables operation of the methods and systems as described herein, including, without limitation, a radioactive ionization source, an electrospray ionization source (ESI), an atmospheric pressure chemical ionization (APCI) source, a corona discharge ionization source, a partial discharge ionization source, an atmospheric pressure photoionization (APPI) source, an atmospheric pressure glow discharge (APGD) source, a direct analysis in real time (DART) source, an atmospheric pressure dielectric barrier discharge (APDBD) source, and an Electron Ionization (EI). In some embodiments of the present disclosure, the ionization source comprises at least one of an APCI source, an APPI source, an ESI source and a DART source. Some embodiments of the present disclosure are configured to operate at sub-atmospheric pressures. Such embodiments include an ionization source that is, without limitation, a chemical ionization (CI) source, a photoionization (PI) source, a glow discharge (GD) source, a dielectric barrier discharge (DBD) source and combinations thereof.

In some embodiments, a method for internal calibration and verification of a detector is disclosed. The method includes calibrating the detector, wherein the calibration includes releasing at least one calibrant from a calibrant chamber in flow communication with the detector, and verifying the calibration, wherein the verification includes releasing at least one verification substance from a verification chamber in flow communication with the detector.

In some embodiments, a method for internal calibration, verification, and sensitivity checking of a detector is disclosed. The method includes calibrating the detector, wherein the calibration includes releasing at least one calibrant from a calibrant chamber in flow communication with the detector, verifying the calibration, wherein the verification includes releasing at least one verification substance from a verification chamber in flow communication with the detector, and checking the sensitivity of the detector, wherein the sensitivity checking includes releasing at least one sensitivity substance from a sensitivity chamber in flow communication with the detector.

In some embodiments, a method for internal calibration and sensitivity checking of a detector is disclosed. The method includes calibrating the detector, wherein the calibration includes releasing at least one calibrant from a calibrant chamber in flow communication with the detector, and checking the sensitivity of the detector, wherein the sensitivity checking includes releasing at least one sensitivity substance from a sensitivity chamber in flow communication with the detector.

Figure 1:
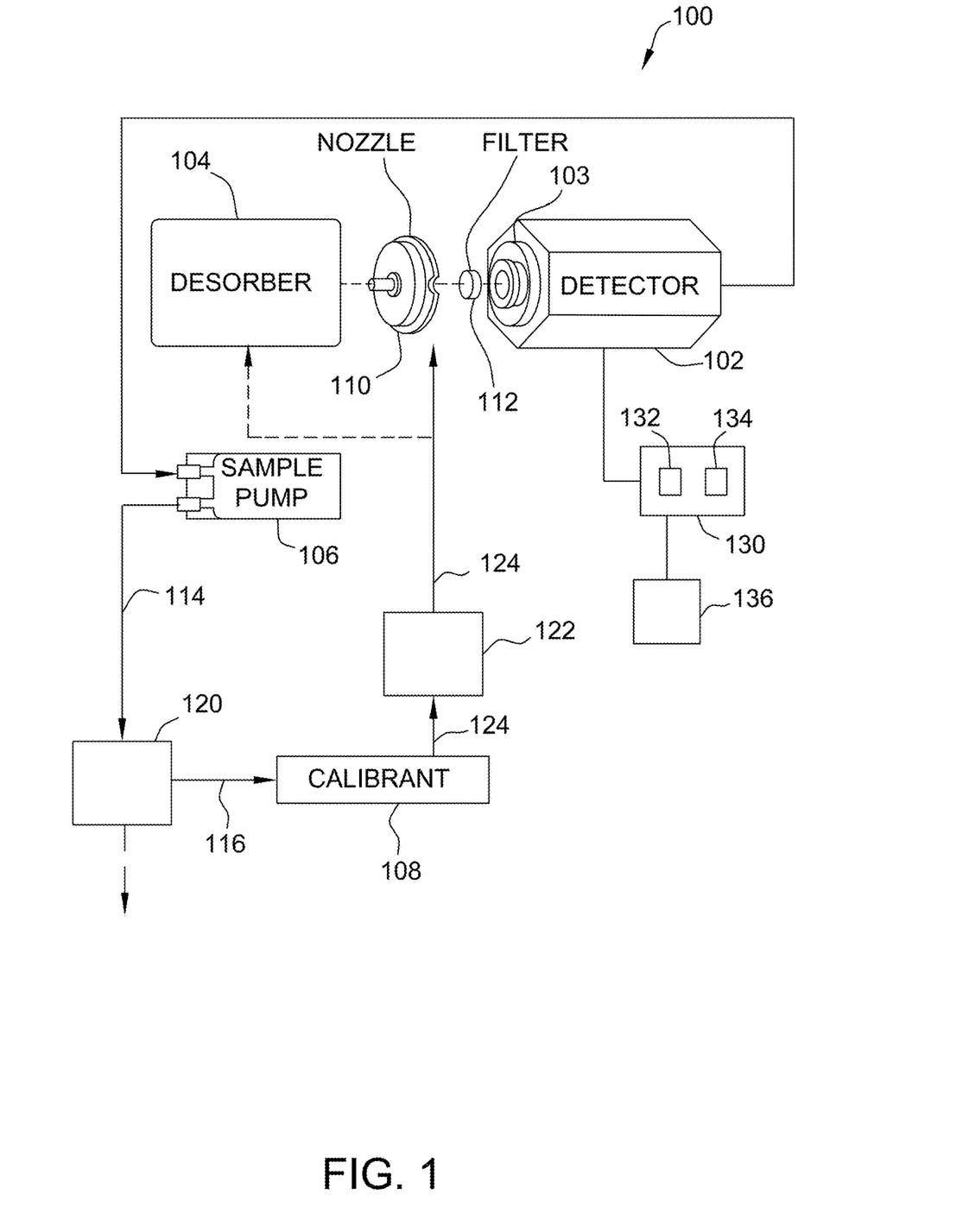
FIG. 1 is a schematic diagram of an exemplary embodiment of a detection system including an internal calibrant chamber in accordance with the present disclosure.

FIG. 1 is a schematic diagram of an exemplary embodiment of a detection system 100. In the illustrated embodiment, detection system 100 includes a detector 102, a desorber 104, a sample pump 106, and a calibrant chamber 108. Detection system 100 further includes a nozzle 110 and a filter 112 in serial flow communication with desorber 104 and detector 102.

Detector 102 is configured to detect and identify constituents in a sample input thereto. For example, in some embodiments, detector 102 is configured to detect one or more substances of interest in a sample gas, such as one or more volatile or non-volatile substances of interest. Detector 102 includes a detector inlet 103 through which substances enter detector 102. It should be understood that where reference is made to a substance entering or flowing into detector 102, those substances enter detector 102 through detector inlet 103.

Sample pump 106 is in flow communication with calibrant chamber 108 via a valve 120. Sample pump 106 is also in flow communication with detector 102 via valve 120. In the illustrated embodiment, valve 120 includes a three-way valve 120, such that, based on a position of valve 120, gas 114 output from sample pump 106 will flow through valve 120 to calibrant chamber 108, will flow through valve 120 to an exhaust outlet, or will not flow through valve 120.

When detection system 100 is operating to calibrate detector 102, valve 120 is positioned such that gas from sample pump 106 flows through valve 120 and through calibrant chamber 108. In some embodiments, this gas is referred to as a "carrier gas" 116. Carrier gas 116 includes at least one of ambient air, purified air, dried air, purified nitrogen, and combinations thereof. In the exemplary embodiment, carrier gas 116 has a flow rate (e.g., from sample pump 106) of from about 5 mL/min to about 5000 mL/min, from about 5 mL/min to about 1000 mL/min, from about 10 mL/min to about 100 mL/min, or from about 25 mL/min to about 50 mL/min. Carrier gas 116 flows through calibrant chamber 108 to "pick up" the calibrant therein and actively delivers the calibrant to detector 102. The combination of carrier gas 116 and the calibrant carried therein is referred to herein as "calibrant gas" 124. Calibrant chamber 108 is in flow communication with detector 102 via a valve 122. In the illustrated embodiment, valve 122 includes a two-way valve 122, such that, based on a position of valve 122, calibrant gas 124 will flow through valve 122 to detector 102 or will not flow through valve 122. To calibrate detector 102, valve 122 is positioned such that calibrant gas 124 flows through valve 122 and to detector 102 for detection of the calibrant. Having internal calibrant chamber 108 enables detection system 100 to use less calibrant than alternative detection systems employing external traps, as detection system 100 is designed to channel the calibrant gas 124 directly to detector 102. Additionally or alternatively, detection system 100 channels the calibrant gas 124 through desorber 104 to detector 102.

In the exemplary embodiment, the calibrant includes at least one of Dibenzylamine, Diethylphenylmalonate, Di-isopropylphenol, 2,4-Dimethylpyridine, Dioctylphthalate, Dinitrotoluene, Dipropylene glycol monomethylether, 2,6-Di-t-butylpyridine, Ethyl salicylate, Hexachloroethane, Hexaphenylbenzene, 4-Methyl-2,6-di-tert-butyl phenol, Methyl salicylate, Nicotinamide, 4-Nitrobenzonitrile, 5-Nitrovanillin, Pentachloroethane, Trihexylamine, and combinations thereof. Whatever particular substance the calibrant is, the calibrant is "known" to detector 102 (e.g., to an operator thereof) prior to calibration of detector 102 using the calibrant. Detector 102 compares a detected signal of the calibrant to a "library" of expected signals representative of different substances, including the calibrant. Detector 102 then adjusts the detected signal by at least a portion of a "calibration unit" in order to match the detected signal to the expected signal for the calibrant. It should be understood that the calibration unit is an arbitrary unit of measure specific to a particular calibration, and accordingly, reference to "one," "more than one," "less than one," and/or "a portion of" a "calibrated unit" may reference the same amount of absolute time. Subsequent detected signals (e.g., sample signals of unknown substances) are then adjusted by same amount (e.g., the at least a portion of the calibration unit) in order to accurately compare the detected (sample) signals to the library of substances for identification of constituents of a sample.

In some embodiments, calibrant chamber 108 includes from about 10 mg to about 500 g of the calibrant. In some embodiments, calibrant chamber 108 includes from about 50 mg to about 250 g of the calibrant, from about 25 mg to about 100 g of the calibrant, or from about 20 mg to about 50 g of the calibrant. More specifically, in some embodiments, calibrant chamber 108 includes from about 0.1 g to about 10 g of the calibrant.

In some embodiments, calibrant chamber 108 includes a permeation tube (not specifically shown) including the calibrant. The permeation tube is configured to emit the calibrant at a particular, predetermined rate. In some embodiments, the calibrant is emitted from the permeation tube at an emission rate of from about 0.4 µg/min to about 30 µg/min. In some embodiments, the calibrant is emitted from the permeation tube at an emission rate of from about 0.5 µg/min to about 25 µg/min, from about 0.75 µg/min to about 20 µg/min, or from about 0.9 µg/min to about 10 µg/min. In some embodiments, the calibrant is emitted from the permeation tube at an emission rate of from about 1 µg/min to about 2 µg/min. In other embodiments, calibrant chamber 108 includes a control valve (not specifically shown) configured to release the calibrant at a particular, predetermined rate. In some embodiments, the control valve releases the calibrant at an emission rate of from about 0.4 µg/min to about 30 µg/min. In some embodiments, the control valve releases the calibrant at an emission rate of from about 0.5 µg/min to about 25 µg/min, from about 0.75 µg/min to about 20 µg/min, or from about 0.9 µg/min to about 10 µg/min. In some embodiments, the control valve releases the calibrant at an emission rate of from about 1 µg/min to about 2 g/min. Carrier gas 116 flows into calibration chamber 108 and "picks up" the calibrant released from the permeation tube and/or by the control valve for analysis by detector 102 and calibration of the detector 102.

In some embodiments, calibration of detector 102 includes ionization of the calibrant in calibrant gas 124. Detector 102 detects and records at least one mobility spectrum of the ionized calibrant. In some embodiments, detector 102 additionally or alternatively detects and records at least one differential mobility spectrum and/or mass spectrum, depending upon the type of detector 102. Accordingly, where "mobility spectrum" is used herein, it should be understood to refer generally to any of these spectra. In the exemplary embodiment, the mobility spectra are plotted on axes corresponding to a drift time and a "count" or "magnitude". Where other types of spectra are detected, one or more of the axes correspond to other characteristics, such as compensation voltage or mass. Drift time is an inherent characteristic of a substance. Therefore, detecting a drift time of a substance enables identification of that substance. Each mobility spectrum includes at least one peak, wherein a particular peak of the mobility spectrum corresponds to the detected calibrant. Detector 102 identifies the drift time associated with the peak, and adjusts the detected drift time of the peak to a known drift time associated with the calibrant.

In some embodiments, detector 102 accesses a library of "known" or "expected" signals or mobility spectra, each spectrum associated with a particular substance. These known mobility spectra are developed by performing a "base calibration" for each substance in the library. The base calibration includes analyzing a known mobility spectrum for each known substance, or, more specifically, analyzing and identifying at least one peak position of the known substance. The known mobility spectra, including the corresponding peak positions, are stored in the library. Detector 102 identifies the known spectrum for the calibrant and adjusts the detected drift time of the detected calibrant peak to match a known drift time associated with a known calibrant peak. For example, in some embodiments, detector 102 shifts the peak up or down a drift time axis by X ms. Detector 102 records this adjustment (e.g., +X ms) as one or more calibration unit(s).

In some embodiments, detector 102 is calibrated at fixed intervals. Moreover, in some embodiments, the fixed intervals are pre-determined, for example, by an operator (not shown) of detection system 100 and/or by pre-programming detection system 100. In some embodiments, the fixed interval is between about 10 minutes and about 24 hours, between about 15 minutes and about 8 hours, between about 30 minutes and about 4 hours, between about 1 hour and about 3 hours, about 2 hours, or about 30 minutes. In some embodiments, the fixed interval is "flexible," in that additional calibrations are performed before the fixed interval has fully elapsed. For example, in some embodiments, detection system 100 is pre-programmed to initiate calibration in the event of a pressure change outside of a certain threshold. As another example, detection system 100 is pre-programmed to shorten one or more intervals if a quality of the calibration is low (e.g., low confidence in the calibration results or poor verification). Additionally or alternatively, detector 102 is calibrated "on-demand," at a time determined by a user (e.g., an operator) of detection system 100. For example, in some embodiments, detector 102 is calibrated on a sample-by-sample basis. In some embodiments, detector 102 is calibrated substantially continuously, for example, before and/or after each sample is analyzed.

In some embodiments, a temperature of calibrant chamber 108 is maintained before, during, and/or after calibration of detector 102. More particularly, in certain embodiments, the temperature of calibrant chamber 108 is maintained between about 0° C. and about 200° C., between about 10° C. and about 150° C., between about 15° C. and about 100° C., or between about 20° C. and about 50° C. The temperature is maintained within calibrant chamber 108 by at least one of heating, cooling, and combinations thereof. For example, in some embodiments, detection system 100 includes one or more heating elements and/or cooling elements (not shown), such as heaters, fans, heating/cooling blocks, and/or any other heating/cooling elements. Additionally or alternatively, the temperature is maintained passively, for example, at an ambient temperature of an environment around detection system 100.

When detection system 100 is operating to detect and identify one or more unknown constituents of a sample gas, valve 120 is positioned such that gas 114 from sample pump 106 flows through valve 120, to a sample input (not shown), and, in some embodiments, to desorber 104. Desorber 104 (if present) vaporizes the sample and channels the vaporized sample through nozzle 110 and filter 112 to detector 102. Detector 102 analyzes the vaporized sample to identify any substances of interest therein.

In the illustrated embodiment, detection system 100 further includes a computing device 130. Although computing device 130 is illustrated as remote from detector 102 and in communication therewith, it should be understood that, in some embodiments, computing device 130 is integral to detector 102. In some embodiments, computing device 130 includes a memory device 132 and a processor 134 operatively coupled to memory device 132 for executing instructions. In some embodiments, executable instructions are stored in the memory device 132. Computing device 130 is configurable to perform one or more operations described herein by programming processor 134. For example, in some embodiments, processor 134 is programmed by encoding an operation as one or more executable instructions and providing the executable instructions in memory device 132. In the exemplary embodiment, memory device 132 is one or more devices that enable storage and retrieval of information such as executable instructions and/or other data. Memory device 132 includes one or more computer readable media in some embodiments.

Memory device 132 is configured to store a pre-programmed library of mobility spectra, each mobility spectrum associated with one substance of a plurality of substances. Memory device 132 may further store associated drift times, alarm limits, detection history, calibration profiles and history (e.g., verification history) for detector 102, and/or any other type data in some embodiments. In the exemplary embodiment, computing device 130, including memory device 132, includes, without limitation, sufficient computer-readable/executable instructions, sufficient data and data structures, algorithms, and commands to facilitate detection of substance(s) introduced into detector 102 (e.g., a sample, the calibrant, the verification substance, and/or the sensitivity substance).

In the exemplary embodiment, substance detection system 100 further includes an operator presentation and/or control interface 136 coupled to computing device 130. Interface 136 presents data, such as mobility spectra, calibration procedures, verification outcomes, and/or sensitivity check outcomes. In some embodiments, interface 136 includes one or more display devices. In some embodiments, interface 136 presents an audible and/or graphical notification upon detection of a substance of interest. Also, in some embodiments, interface 136 facilitates control of computing device 130 and manual data input into computing device 130. Furthermore, in some embodiments, computing device 130 is coupled in communication with one or more other devices, such as another computing device 130, locally or remotely. As such, in some embodiments, substance detection system 100 is networked with other systems and devices such that data transmitted across portions of system 100 is accessed by any device capable of accessing computing device 130 including, without limitation, desktop computers, laptop computers, and personal digital assistants (PDAs) (neither shown).

As used herein, the term "computer" and related terms, e.g., "computing device", are not limited to integrated circuits referred to in the art as a computer, but broadly refers to a microcontroller, a microcomputer, a programmable logic controller (PLC), an application specific integrated circuit, and other programmable circuits, and these terms are used interchangeably herein. Further, as used herein, the terms "software" and "firmware" are interchangeable, and include any computer program stored in memory for execution by personal computers, workstations, clients and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

Figure 2:
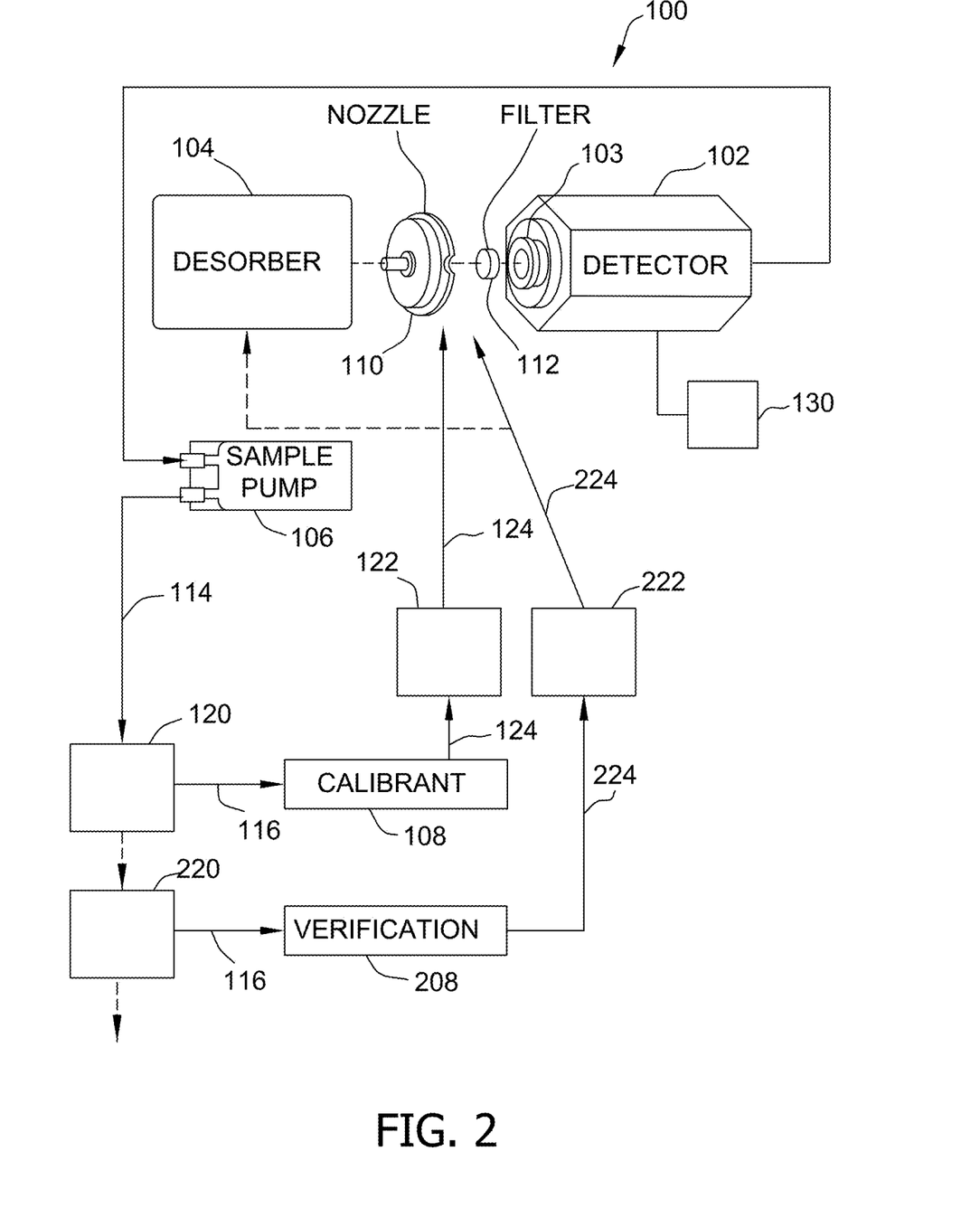
FIG. 2 is a schematic diagram of an exemplary embodiment of a detection system including an internal calibrant chamber and a verification chamber.

FIG. 2 is a schematic diagram of another exemplary embodiment of detection system 100, as shown in FIG. 1. More particularly, detection system 100 is shown to further include a verification chamber 208.

In the illustrated embodiment, sample pump 106 is in flow communication with calibrant chamber 108 via valve 120, and is in flow communication with verification chamber 208 via a valve 220. In the illustrated embodiment, valve 120 includes a three-way valve 120, such that, based on a position of valve 220, gas 114 output from sample pump 106 will flow through valve 120 to calibrant chamber 106, will flow through valve 120 to valve 220, or will not flow through valve 120. Moreover, valve 220 includes a three-way valve 220, such that, based on a position of valve 220, gas 114 output from sample pump 106 through valve 220 will flow through valve 220 to verification chamber 208, will flow through valve 220 to an exhaust outlet, or will not flow through valve 220.

When detection system 100 is operating to verify a previous calibration of detector 102, valve 220 is positioned such that carrier gas 116 from sample pump 106 flows through valve 120, through valve 220, and through verification chamber 108. Carrier gas 116 flows through verification chamber 208 to "pick up" the verification substance therein and actively deliver the verification substance to detector 102. The combination of carrier gas 116 and the verification substance carried therein is referred to herein as "verification gas" 224. Verification chamber 208 is in flow communication with detector 102 via a valve 222. In the illustrated embodiment, valve 222 includes a two-way valve 222, such that, based on a position of valve 222, verification gas 224 will flow through valve 222 to detector 102 or will not flow through valve 222. To verify a previous calibration of detector 102, valve 222 is positioned such that verification gas 224 flows through valve 222 and to detector 102 for detection of the verification substance. Having internal verification chamber 208 enables detection system 100 to use less verification substance than alternative detection systems employing external traps, as detection system 100 is designed to channel the verification gas 224 directly to detector 102. Additionally or alternatively, detection system 100 channels the calibrant gas 124 through desorber 104 to detector 102.

In the exemplary embodiment, the verification substance includes at least one of Dibenzylamine, Diethylphenylmalonate, Diisopropylphenol, 2,4-Dimethylpyridine, Dioctylphthalate, Dinitrotoluene, Dipropylene glycol monomethylether, 2,6-Di-t-butylpyridine, Ethyl salicylate, Hexachloroethane, Hexaphenylbenzene, 4-Methyl-2,6-di-tert-butyl phenol, Methyl salicylate, Nicotinamide, 4-Nitrobenzonitrile, 5-Nitrovanillin, Pentachloroethane, Trihexylamine, and combinations thereof. In some embodiments, the calibrant and the verification substance include the same substance. In other embodiments, the calibrant and the verification substance include at least one different substance. Whatever particular substance the verification substance is, the verification substance is "known" to detector 102 (e.g., to an operator thereof) prior to verification of the calibration of detector 102 using the verification substance. Detector 102 generates a detected signal of the verification substance, adjusts the detected signal by the calibration unit, and compares the adjusted signal to a "library" of expected signals representative of different substances, including the verification substance. If the adjusted signal is within a particular range of the expected signal (e.g., with one standard deviation), the calibration of detector 102 is considered to be verified. If the calibration is not verified, in some embodiments, an operator of detection system 100 repeats the calibration process described above.

In some embodiments, verification chamber 208 includes from about 10 mg to about 500 g of the verification substance. In some embodiments, verification chamber 208 includes from about 50 mg to about 250 g of the verification substance, from about 25 mg to about 100 g of the verification substance, or from about 20 mg to about 50 g of the verification substance. More specifically, in some embodiments, verification chamber 208 includes from about 0.1 g to about 10 g of the verification substance.

In some embodiments, verification chamber 208 includes a permeation tube (not specifically shown) including the verification substance. The permeation tube is configured to emit the verification substance at a particular, predetermined rate. The verification substance is emitted from the permeation tube at an emission rate of from about 0.4 µg/min to about 30 µg/min. In some embodiments, the verification substance is emitted from the permeation tube at an emission rate of from about 0.5 µg/min to about 25 µg/min, from about 0.75 µg/min to about 20 µg/min, or from about 0.9 µg/min to about 10 µg/min. In some embodiments, the verification substance is emitted from the permeation tube at an emission rate of from about 1 µg/min to about 2 µg/min. In other embodiments, verification chamber 208 includes a control valve (not specifically shown) configured to release the verification substance at a particular, predetermined rate. The control valve releases the verification substance at an emission rate of from about 0.4 µg/min to about 30 µg/min. In some embodiments, the control valve releases the verification substance at an emission rate of from about 0.5 µg/min to about 25 µg/min, from about 0.75 µg/min to about 20 µg/min, or from about 0.9 µg/min to about 10 µg/min. In some embodiments, the control valve releases the verification substance at an emission rate of from about 1 µg/min to about 2 µg/min. Carrier gas 116 flows into verification chamber 208 and "picks up" the verification substance released from the permeation tube and/or by the control valve for analysis by detector 102 and verification of the calibration of the detector 102.

In some embodiments, verification of the calibration of detector 102 includes ionization of the verification substance in verification gas 224. Detector 102 detects and records at least one mobility spectrum (and/or differential mobility or mass spectrum) of the ionized verification substance. In the exemplary embodiment, the mobility spectrum is plotted on axes corresponding to drift time and count. The mobility spectrum is automatically shifted on the drift time axis (and/or a compensation voltage axis or mass axis, according to a type of detector 102) according the calibration unit(s), determined above. The mobility spectrum includes a peak, which, once the mobility spectrum is adjusted, should correspond to the detected verification substance. Detector 102 identifies the drift time associated with the adjusted peak. In some embodiments, detector 102 accesses the library of known mobility spectra. Detector 102 identifies the known spectrum for the verification substance and determines whether the adjusted peak is within a particular range of the known peak for the verification substance. Detector 102 further records the adjusted and verified mobility spectrum and drift time. If the adjusted peak is within a defined range of the known peak, the calibration of detector 102 is verified. If the calibration is not verified, in some embodiments, an operator of detection system 100 repeats the calibration process described above.

In some embodiments, the verification of the calibration of detector 102 is performed at fixed intervals. Moreover, in some embodiments, the fixed intervals are pre-determined, for example, by an operator (not shown) of detection system 100 and/or by pre-programming detection system 100. In some embodiments, the fixed interval is between about 10 minutes and about 24 hours, between about 15 minutes and about 8 hours, between about 30 minutes and about 4 hours, between about 1 hour and about 3 hours, about 30 minutes, or about 2 hours. In some embodiments, the fixed interval is "flexible," in that additional verifications is performed before the fixed interval has fully elapsed. For example, in some embodiments, detection system 100 is pre-programmed to shorten one or more intervals if the verification process indicates low confidence in the calibration. Additionally or alternatively, the calibration of detector 102 is verified "on-demand," at a time determined by a user (e.g., an operator) of detection system 100. Additionally or alternatively, the calibration of detector 102 is verified substantially continuously (e.g., without substantial pause) after each calibration of detector 102. In some embodiments, the calibration of detector 102 is verified within a predetermined amount of time after the calibration. The predetermined amount of time, in various embodiments, is between about 10 seconds to about 1 day after calibration, between about 15 seconds to about 12 hours after calibration, between about 30 seconds to about 2 hours after calibration, between about 45 seconds to about 10 minutes after calibration, between about 1 minute to about 5 minutes after calibration, or between about 1 minute and about 2 minutes after calibration. Additionally or alternatively, the calibration of detector 102 is verified on a sample-by-sample basis.

In some embodiments, a temperature of verification chamber 208 is maintained before, during, and/or after verification of the calibration of detector 102. More particularly, in certain embodiments, the temperature of verification chamber 208 is maintained between about 0° C. and about 200° C., between about 10° C. and about 150° C., between about 15° C. and about 100° C., or between about 20° C. and about 50° C. The temperature is maintained within verification chamber 208 by at least one of heating, cooling, and combinations thereof. For example, in some embodiments, detection system 100 includes one or more heating elements and/or cooling elements (not shown), such as heaters, fans, heating/cooling blocks, and/or any other heating/cooling elements. Additionally or alternatively, the temperature of verification chamber 208 is maintained passively, for example, at an ambient temperature of an environment around detection system 100.

Figure 3:
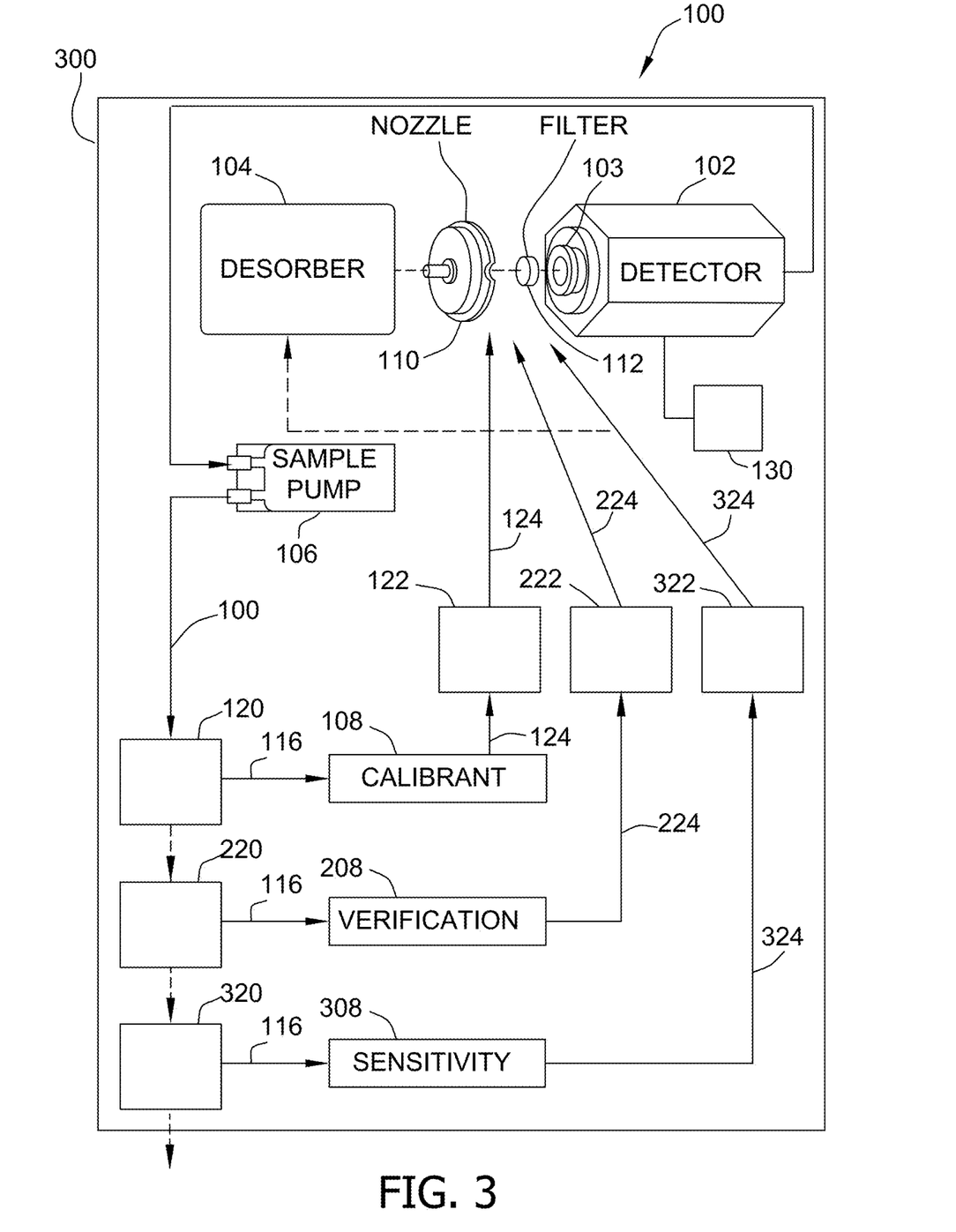
FIG. 3 is a schematic diagram of an exemplary embodiment of a detection system including an internal calibrant chamber, a verification chamber, and a sensitivity chamber.

FIG. 3 is a schematic diagram of another exemplary embodiment of detection system 100, as shown in FIGS. 1 and 2. More particularly, detection system 100 is shown to further include a sensitivity chamber 308, as well as a housing 300. In the illustrated embodiment, housing 300 contains all components of detection system 100, including detector 102, calibrant chamber 108, verification chamber 208, and sensitivity chamber 308.

In the illustrated embodiment, sample pump 106 is in flow communication with calibrant chamber 108 via valve 120, is in flow communication with verification chamber 208 via valve 220, and is in flow communication with sensitivity chamber 308 via a valve 320. In the illustrated embodiment, valve 120 includes a three-way valve 120, such that, based on a position of valve 120, gas 114 output from sample pump 106 will flow through valve 120 to calibrant chamber 108, will flow through valve 120 to valve 220, or will not flow through valve 120. Moreover, valve 220 includes a three-way valve 220, such that, based on a position of valve 220, gas 114 output from sample pump 106 through valve 220 will flow through valve 220 to verification chamber 208, will flow through valve 220 to valve 320, or will not flow through valve 220. In addition, valve 320 includes a three-way valve 320 such that, based on a position of valve 320, gas 114 output from sample pump 106 will flow through valve 320 to sensitivity chamber 308, will flow through valve 320 to detector 102, or will not flow through valve 320.

When detection system 100 is operating to check a sensitivity of detector 102, valves 120, 220, and 320 are positioned such that carrier gas 116 from sample pump 106 flows through valve 120, through valve 220, through valve 320 and through sensitivity chamber 308. Carrier gas 116 flows through sensitivity chamber 308 to "pick up" the sensitivity substance therein and actively deliver the sensitivity substance to detector 102. The combination of carrier gas 116 and the sensitivity substance carried therein is referred to herein as "sensitivity gas" 324. Sensitivity chamber 308 is in flow communication with detector 102 via a valve 322. In the illustrated embodiment, valve 322 includes a two-way valve 322, such that, based on a position of valve 322, sensitivity gas 324 will flow through valve 322 to detector 102 or will not flow through valve 322. To check the sensitivity of detector 102, valve 322 is positioned such that sensitivity gas 324 flows through valve 322 and to detector 102 for detection of the sensitivity substance. Having internal sensitivity chamber 308 enables detection system 100 to use less sensitivity substance than alternative detection systems employing external traps, as detection system 100 is designed to channel the sensitivity gas 324 directly to detector 102. Additionally or alternatively, detection system 100 channels the calibrant gas 124 through desorber 104 to detector 102.

In the exemplary embodiment, the sensitivity substance includes at least one of Dibenzylamine, Diethylphenylmalonate, Di-isopropylphenol, 2,4-Dimethylpyridine, Dioctylphthalate, Dinitrotoluene, Dipropylene glycol monomethyl ether, 2,6-Di-t-butylpyridine, Ethyl salicylate, Hexachloroethane, Hexaphenylbenzene, 4-Methyl-2,6-di-tert-butyl phenol, Methyl salicylate, Nicotinamide, 4-Nitrobenzonitrile, 5-Nitrovanillin, Pentachloroethane, Trihexylamine, and combinations thereof. In some embodiments, the calibrant and the sensitivity substance include the same substance. In other embodiments, the calibrant and the sensitivity substance include at least one different substance. In some embodiments, the verification substance and the sensitivity substance include the same substance. In other embodiments, the verification substance and the sensitivity substance include at least one different substance. Whatever particular substance the sensitivity substance is, the sensitivity substance is "known" to detector 102 (e.g., to an operator thereof) prior to checking the sensitivity of detector 102 using the sensitivity substance. Moreover, the amount of the sensitivity substance introduced into detector 102 is typically known. Detector 102 generates a detected signal of the sensitivity substance. If the signal has an appropriate magnitude according to the known amount of the sensitivity substance introduced into detector 102, the sensitivity of detector 102 is considered to be confirmed. In some embodiments, if the sensitivity is not confirmed (e.g., the sensitivity substance is not detected), an operator of detection system 100 requests service for detection system 100.

In some embodiments, sensitivity chamber 308 includes from about 10 mg to about 500 g of the sensitivity substance. In some embodiments, sensitivity chamber 308 includes from about 50 mg to about 250 g of the sensitivity substance, from about 25 mg to about 100 g of the sensitivity substance, or from about 20 mg to about 50 g of the sensitivity substance. More specifically, in some embodiments, sensitivity chamber 308 includes from about 0.1 g to about 10 g of the sensitivity substance.

In some embodiments, sensitivity chamber 308 includes a permeation tube (not specifically shown) including the sensitivity substance. The permeation tube is configured to emit the sensitivity substance at a particular, predetermined rate. The sensitivity substance is emitted from the permeation tube at an emission rate of from about 0.4 µg/min to about 30 µg/min. In some embodiments, the sensitivity substance is emitted from the permeation tube at an emission rate of from about 0.5 µg/min to about 25 µg/min, from about 0.75 µg/min to about 20 µg/min, or from about 0.9 µg/min to about 10 µg/min. In some embodiments, the sensitivity substance is emitted from the permeation tube at an emission rate of from about 1 µg/min to about 2 µg/min.

In other embodiments, sensitivity chamber 308 includes a control valve (not specifically shown) configured to release the sensitivity substance at a particular, predetermined rate. The control valve releases the sensitivity substance at an emission rate of from about 0.4 µg/min to about 30 µg/min. In some embodiments, the control valve releases the sensitivity substance at an emission rate of from about 0.5 µg/min to about 25 µg/min, from about 0.75 µg/min to about 20 µg/min, or from about 0.9 µg/min to about 10 µg/min. In some embodiments, the control valve releases the sensitivity substance at an emission rate of from about 1 µg/min to about 2 µg/min. Carrier gas 116 flows into sensitivity chamber 308 and "picks up" the sensitivity substance released from the permeation tube and/or by the control valve for analysis by detector 102 and for checking the sensitivity of the detector 102. In the exemplary embodiment, whatever the flow rate of the sensitivity substance into the sensitivity chamber 308, the amount or quantity of the sensitivity substance carried in carrier gas (and/or a concentration of the sensitivity substance in the carrier gas) is "known," for example, by the operator, such that it is determined whether the detector 102 is sensitive enough (e.g., to comply with business/client and/or legal requirements).

In some embodiments, checking the sensitivity of detector 102 includes ionization of the sensitivity substance in sensitivity gas 324. Detector 102 detects and records at least one mobility spectrum (and/or differential mobility or mass spectrum) of the ionized sensitivity substance. In the exemplary embodiment, the mobility spectrum is plotted on axes corresponding to drift time and count. The mobility spectrum is shifted on the drift time axis (and/or a compensation voltage axis or mass axis, according to a type of detector 102) according the calibration unit(s), determined above. The mobility spectrum includes a peak, which, once the mobility spectrum is adjusted, should correspond to the detected sensitivity substance. Detector 102 identifies the drift time associated with the adjusted peak. In some embodiments, detector 102 accesses the library of known mobility spectra. Detector 102 identifies the known spectrum for the sensitivity substance and determines whether the peak of the mobility spectrum has an appropriate intensity from the sensitivity substance based upon the known amount of the sensitivity substance channeled to detector 102 in sensitivity gas 324. In some embodiments, detector 102 analyzes the peak quantitatively, for example, whether the intensity of the peak is within a particular range. In some embodiments, detector 102 analyzes the peak proportionally, for example, whether the peak of the sensitivity substance is proportional to the peak of a substance of carrier gas 116, in accordance with the known amount/proportion of sensitivity substance within sensitivity gas 324. In some embodiments, detector 102 analyzes the peak qualitatively, for example, whether the intensity of the peak is above a "detection" threshold, indicating that the sensitivity substance was successfully detected. If the peak of the mobility spectrum is quantitatively, proportionally, qualitatively, and/or otherwise determined to be appropriate, the sensitivity of detector 102 is confirmed or verified. In some embodiments, detector 102 compares an intensity of the peak and/or any other characteristic of the mobility spectrum to a number of preselected detection criteria, which initiates an alarm state that is evaluated by detector 102 (e.g., using one or more software applications). Rather than imposing a binary response to one threshold, detector 102 is programmed to evaluate an alarm strength of the alarm state, wherein a low alarm strength represents a lower level of detection or lower confidence in a detection. A higher alarm strength represents a higher level of detection or higher confidence in a detection.

In some embodiments, the sensitivity check of detector 102 is performed at fixed intervals. Moreover, in some embodiments, the fixed intervals are pre-determined, for example, by an operator (not shown) of detection system 100 and/or by pre-programming detection system 100. In some embodiments, the fixed interval is between about 10 minutes and about 24 hours, between about 15 minutes and about 8 hours, between about 30 minutes and about 4 hours, between about 1 hour and about 3 hours, about 30 minutes, or about 2 hours. In some embodiments, the fixed interval is "flexible," in that additional sensitivity checks are performed before the fixed interval has fully elapsed. For example, in some embodiments, detection system 100 is pre-programmed to shorten one or more intervals if the sensitivity check indicates low confidence in detector 102 sensitivity. Additionally or alternatively, the sensitivity of detector 102 is checked "on-demand," at a time determined by a user (e.g., an operator) of detection system 100. Additionally or alternatively, the sensitivity of detector 102 is checked after each calibration of detector 102. In some embodiments, the sensitivity of detector 102 is checked substantially continuously (e.g., without substantial pause) after each calibration and/or verification of calibration of detector 102. In some embodiments, the sensitivity of detector 102 is checked within a predetermined amount of time after the calibration and/or the verification of the calibration. The predetermined amount of time, in various embodiments, is between about 10 seconds to about 1 day after calibration and/or verification, between about 15 seconds to about 12 hours after calibration and/or verification, between about 30 seconds to about 2 hours after calibration and/or verification, between about 45 seconds to about 10 minutes after calibration and/or verification, between about 1 minute to about 5 minutes after calibration and/or verification, or between about 1 minute and about 2 minutes after calibration and/or verification. Additionally or alternatively, the sensitivity of detector 102 is checked on a sample-by-sample basis.

In some embodiments, a temperature of sensitivity chamber 308 is maintained before, during, and/or after checking the sensitivity of detector 102. More particularly, in certain embodiments, the temperature of sensitivity chamber 308 is maintained between about 0° C. and about 200° C., between about 10° C. and about 150° C., between about 15° C. and about 100° C., or between about 20° C. and about 50° C. The temperature is maintained within sensitivity chamber 308 by at least one of heating, cooling, and combinations thereof. For example, in some embodiments, detection system 100 includes one or more heating elements and/or cooling elements (not shown), such as heaters, fans, heating/cooling blocks, and/or any other heating/cooling elements. Additionally or alternatively, the temperature of sensitivity chamber 208 is maintained passively, for example, at an ambient temperature of an environment around detection system 100.

It should be understood that other embodiments of detection system 100 includes different combinations of the calibration chamber 108, verification chamber 208, and sensitivity chamber 308 than are illustrated herein. Moreover, in some embodiments, detection system 100 includes at least one of calibration chamber 108, verification chamber 208, and/or sensitivity chamber 308. It should also be understood that detection system 100 includes additional and/or alternative components in some embodiments. For example, in some embodiments, detection system 100 includes a sample pre-separation component (e.g., a chromatographic pre-separator) to separate a vaporized sample before the sample is channeled into detector 102.

Moreover, in some embodiments, detection system 100 includes one or more additional or alternative components such that one or more of the calibration, calibration verification, and sensitivity check are performed using a method other than the internal method described above. For instance, in one example embodiment, detection system 100 includes a calibration component (not shown) configured to perform calibration of detector 102 other than internally, such as an external calibrant trap. The external calibrant trap includes a calibrant that is introduced to detector 102 through desorber 104. In some embodiments, verification and sensitivity checking of detector 102 is subsequently performed internally, as described herein.

EXAMPLES

The following examples describe or illustrate various embodiments of the present disclosure. Other embodiments within the scope of the appended claims will be apparent to a skilled artisan considering the specification or practice of the disclosure as described herein. It is intended that the specification, together with the Examples, be considered exemplary only, with the scope and spirit of the disclosure being indicated by the claims, which follow the Examples.

Example 1

Calibration

Figure 4:
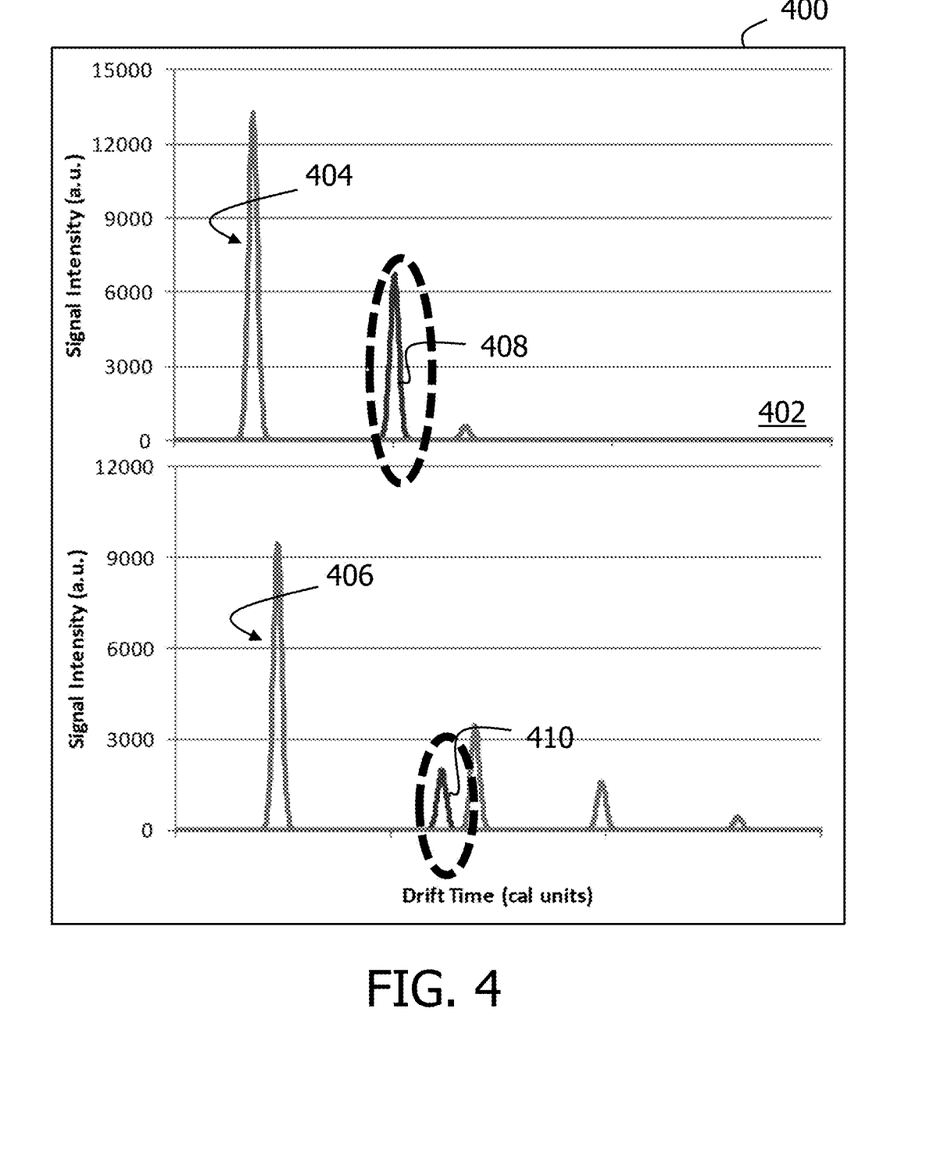
FIG. 4 is an exemplary embodiment of a screen-capture of a calibration process performed by the detection system shown in FIGS. 1-3, in accordance with the present disclosure.
Figure 5:
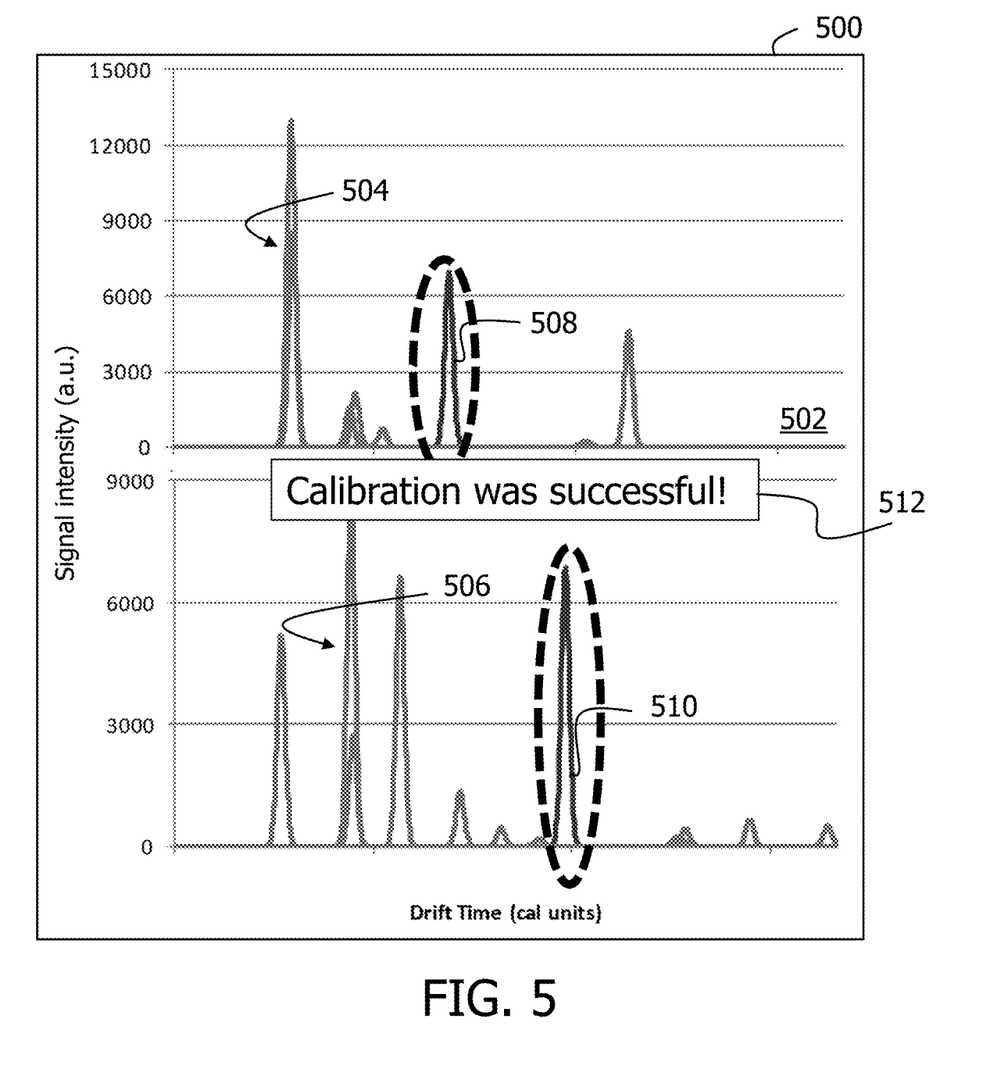
FIG. 5 is an exemplary embodiment of a screen-capture of another calibration process performed by the detection system shown in FIGS. 1-3, in accordance with the present disclosure.

Example 1 is an exemplary embodiment of calibration of detector 102 (shown in FIGS. 1-3) using the systems and methods described herein. In particular, FIG. 4 is an exemplary embodiment of a screen-capture 400 of a calibration process performed by detection system 100 (also shown in FIGS. 1-3), and FIG. 5 is another exemplary embodiment of a screen-capture 500 of a confirmation of another calibration process performed by the detection system 100. In this example, a calibrant gas (e.g., calibrant gas 124) including a carrier gas (e.g., carrier gas 116, both shown in FIGS. 1-3) and a calibrant comprising methyl salicylate was input to detector 102 for detection of the calibrant. Screen-capture 400 and/or 500 represent content displayed, for example, on interface 136 (shown in FIG. 1).

Screen-capture 400 included a plot 402 of two mobility spectra 404, 406. In the illustrated embodiment, the first mobility spectrum 404 is a mobility spectrum of detected negative ions, and the second mobility spectrum 406 is a mobility spectrum of detected positive ions. The x-axis is the flight time of the ions in the drift tube (a "drift time") and as such represents a signature or identity of the substance detected, and the y-axis represents a number of "counts" of the substance detected. Increasing height with respect to the y-axis represents a stronger signal, indicating a higher presence of a substance. Each mobility spectrum 404, 406 included at least one peak. In this example, first mobility spectrum 404 included a first peak 408 representing detection of negative ions of the calibrant. Second mobility spectrum 406 included a second peak 410 representing detection of positive ions of the calibrant.

First peak 408 is located along the x-axis at a first drift time, and second peak 410 is located along the x-axis at a second drift time. Detector 102 accessed a library of known mobility spectra for the calibrant and determined the known negative-ion and positive-ion drift times for calibrant-substance peaks.

Similarly, screen-capture 500 included a plot 502 of two mobility spectra 504, 506 of the detected negative ions and the detected positive ions, respectively. In this example, first mobility spectrum 504 included a first peak 508 representing detection of negative ions of the calibrant. Second mobility spectrum 506 included a second peak 510 representing detection of positive ions of the calibrant. Detector 102 accessed a library of known mobility spectra for the calibrant and determined the known negative-ion and positive-ion drift times for calibrant-substance peaks. In the illustrated embodiment of FIG. 5, to complete the calibration process, detector 102 adjusted peaks 508, 510 such that the adjusted peaks (not shown) correspond to the correct drift times for negative and positive ions, respectively, of the calibrant, according to the library of known mobility spectra. A "calibration successful" dialog 512 is displayed, indicating that the peaks 508, 510 of the mobility spectra 504, 506 were successfully adjusted. Detector 102 recorded the amount or value of the adjustment needed for each of peaks 508, 510 and stored this value as a calibration value or calibration unit. Subsequent detected signals (e.g., when detector 102 is analyzing an unknown substance of interest) were automatically adjusted by these calibration values.

Example 2

Verification

Figure 6:
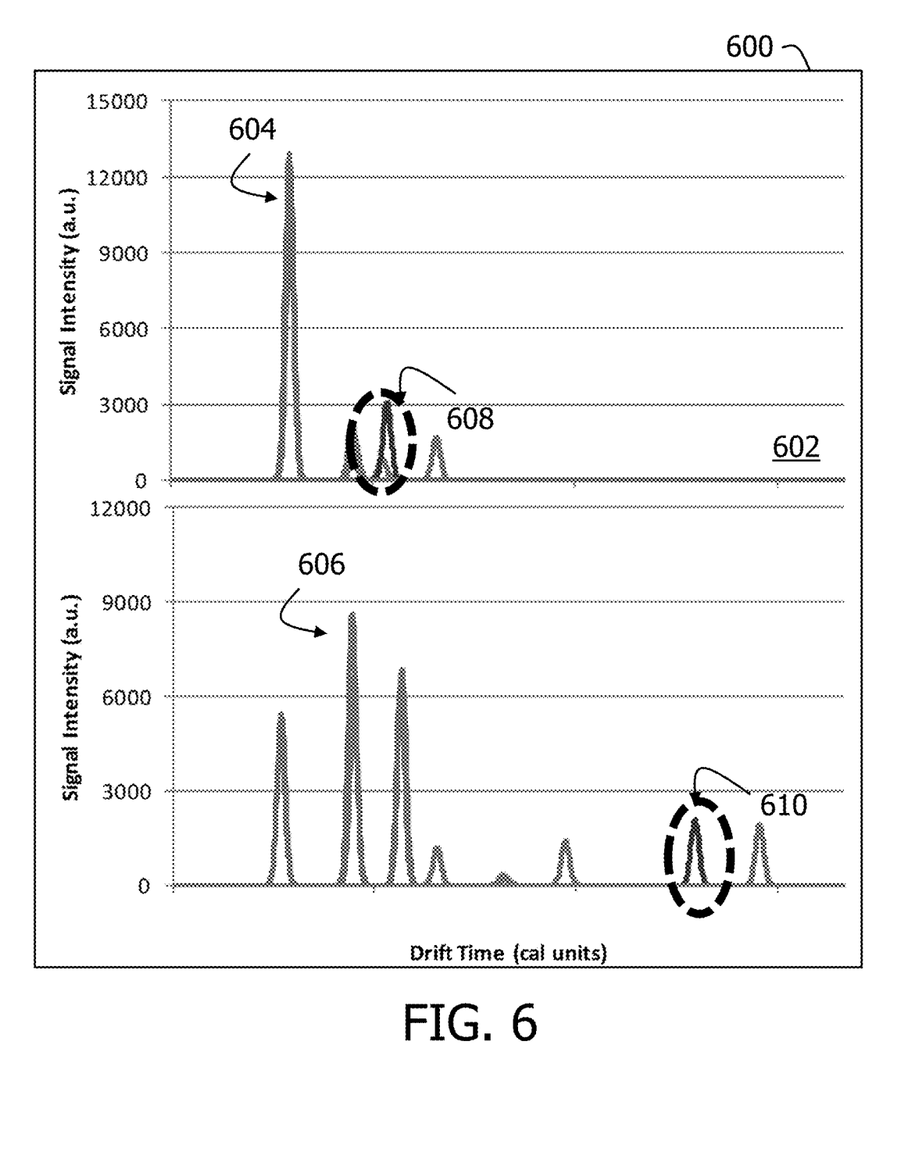
FIG. 6 is an exemplary embodiment of a screen-capture of a verification process performed by the detection system shown in FIGS. 2 and 3 to verify the calibration illustrated in FIG. 5, in accordance with the present disclosure.

Example 2 is an exemplary embodiment of verification of the calibration of detector 102 using the systems and methods described herein. In particular, FIG. 6 is an exemplary embodiment of a screen-capture 600 of a verification process performed by detection system 100. In this example, a verification gas (e.g., verification gas 224, shown in FIGS. 2 and 3) including a carrier gas (e.g., carrier gas 116) and a verification substance comprising methyl salicylate were input to detector 102 for detection of the verification substance. Screen-capture 600 represented content displayed, for example, on interface 136 (shown in FIG. 1).

Screen-capture 600 included a plot 602 of two mobility spectra 604, 606. In the illustrated embodiment, the first mobility spectrum 604 is the mobility spectrum of the negative ions of the carrier gas and verification substance, and the second mobility spectrum 606 is the mobility spectrum of the positive ions of the carrier gas and verification substance. Each mobility spectrum 604, 606 included at least one peak. In this example, first mobility spectrum 604 included a first peak 608 representing detection of negative ions of the verification substance. Second mobility spectrum 606 included a second peak 610 representing detection of positive ions of the verification substance. Detector 102 had adjusted peaks 608, 610 by the calibration units determined in Example 1. In this example, detector 102 had detected peaks 608, 610 representing the verification substance, for example, by accessing the library of known substances and confirming a match of peaks 608, 610 with known peaks of a known mobility spectrum of the verification substance. In some embodiments, detector 102 accordingly displays an alert (not shown). The alert indicates successful verification of the calibration of detector 102, as the adjusted peaks 608, 610 of the verification substance were appropriately detected. If adjusted peaks 608, 610 did not correspond to known peaks of the known mobility spectrum of the verification substance, in some embodiments detector 102 does not display an alert. For instance, in some embodiments, detector 102 displays a "verification unsuccessful" dialog and/or a different alert, and/or produces a sonic alert indicating the verification was unsuccessful, such that the calibration is performed again.

Exemplary embodiments of detection systems for calibrating a detector, verifying the calibration of the detector, and checking the sensitivity of the detector, and methods of operating such systems are not limited to the specific embodiments described herein, but rather, components of systems and/or steps of the methods may be utilized independently and separately from other components and/or steps described herein. For example, the methods may also be used in combination with other systems requiring calibration of a detector, verification of the calibration of the detector, and checks of the sensitivity of the detector, and are not limited to practice with only the substance detection systems and methods as described herein. Rather, the exemplary embodiment is implemented and utilized in connection with many other substance detection applications that are currently configured to determine the presence of substances of interest.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

Some embodiments involve the use of one or more electronic or computing devices. Such devices typically include a processor or controller, such as a general purpose central processing unit (CPU), a graphics processing unit (GPU), a microcontroller, a reduced instruction set computer (RISC) processor, an application specific integrated circuit (ASIC), a programmable logic circuit (PLC), and/or any other circuit or processor capable of executing the functions described herein. The methods described herein may be encoded as executable instructions embodied in a computer readable medium, including, without limitation, a storage device and/or a memory device. Such instructions, when executed by a processor, cause the processor to perform at least a portion of the methods described herein. The above examples are exemplary only, and thus are not intended to limit in any way the definition and/or meaning of the term processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for internally performing a calibration and a verification of a detector in a mobility spectrometer, the method comprising:

performing the calibration of the detector, wherein the calibration comprises releasing at least one calibrant in a form of a gas from at least one calibrant chamber in flow communication with the detector, generating a calibration signal using the at least one calibrant, comparing the calibration signal to an expected signal, and, based on the comparing, determining a calibration unit for use in processing future detected signals;

performing the verification of the calibration, wherein the verification comprises releasing at least one verification substance in a form of a gas from at least one verification chamber in flow communication with the detector, wherein the at least one verification substance has at least one predefined mobility spectrum and wherein the at least one verification chamber and at least one calibrant chamber are separate chambers;

ionizing the at least one verification substance to generate a verification signal;

automatically adjusting at least one mobility spectrum of the at least one ionized verification substance by at least a portion of the calibration unit wherein the at least one mobility spectrum includes at least one peak;

recording the at least one mobility spectrum of the at least one ionized verification substance; and generating a verification signal, adjusting the verification signal using the calibration unit, comparing the adjusted verification signal to an expected signal, and, based on the comparing, verifying the calibration or repeating the calibration.

2. The method of claim 1, wherein the calibration comprises:

ionizing the at least one calibrant to generate the calibration signal; and recording at least one mobility spectrum of the at least one ionized calibrant, wherein the at least one mobility spectrum includes at least one peak.

3. The method of claim 1, wherein the verification further comprises:

verifying an adjusted drift time of the at least one peak; and recording the adjusted drift time.

4. A method for performing a calibration, verification, and sensitivity checking of a detector in a mobility spectrometer, the method comprising:

performing the calibration of the detector, wherein the calibration comprises releasing at least one calibrant in a form of a gas from at least one calibrant chamber in flow communication with the detector, generating a calibration signal using the at least one calibrant, comparing the calibration signal to an expected signal, and determining a calibration unit for use in adjusting future detected signals;

performing the verification of the calibration, wherein the verification comprises releasing at least one verification substance in a form of a gas from at least one verification chamber in flow communication with the detector, wherein the at least one verification substance has at least one predefined mobility spectrum and wherein the at least one verification chamber and at least one calibrant chamber are separate chambers;

ionizing the at least one verification substance to generate the verification signal;

automatically adjusting at least one mobility spectrum of the at least one ionized verification substance by at least a portion of the calibration unit wherein the at least one mobility spectrum includes at least one peak;

recording the at least one mobility spectrum of the at least one ionized verification substance;

comparing the adjusted verification signal to an expected signal; and, based on the comparing, verifying the calibration or repeating the calibration; and, checking the sensitivity of the detector, wherein the sensitivity checking comprises releasing at least one sensitivity substance in a form of a gas from at least one sensitivity chamber in flow communication with the detector.

5. The method of claim 4, wherein releasing the at least one sensitivity substance comprises releasing a predetermined quantity of the at least one sensitivity substance.

6. The method of claim 4, wherein checking the sensitivity comprises:

ionizing the at least one sensitivity substance; and recording at least one mobility spectrum of the at least one ionized sensitivity substance, wherein the at least one mobility spectrum includes at least one peak.

7. The method of claim 6, wherein checking the sensitivity further comprises comparing the at least one mobility spectrum to at least one pre-determined mobility spectrum of the at least one sensitivity substance.

8. The method of claim 4, wherein the calibration comprises:

ionizing the at least one calibrant; and recording at least one mobility spectrum of the at least one ionized calibrant, wherein the at least one mobility spectrum includes at least one peak.

9. A method for performing a calibration, a verification, and a sensitivity check of a detector in a mobility spectrometer, the method comprising:

performing the calibration of the detector by releasing at least one calibrant in a form of a gas from at least one calibrant chamber in flow communication with the detector, generating a calibration signal using the at least one calibrant, comparing the calibration signal to an expected signal, and determining a calibration unit for use in adjusting future detected signals;

performing the verification of the calibration, wherein the verification comprises releasing at least one verification substance in a form of a gas from at least one verification chamber in flow communication with the detector, wherein the at least one verification substance has at least one predefined mobility spectrum;

ionizing the at least one verification substance to generate a verification signal;

automatically adjusting at least one mobility spectrum of the at least one ionized verification substance by at least a portion of the calibration unit wherein the at least one mobility spectrum includes at least one peak;

recording the at least one mobility spectrum of the at least one ionized verification substance;

comparing the adjusted verification signal to an expected signal; and, based on the comparing, verifying the calibration or repeating the calibration; and performing the sensitivity check of the detector, wherein the sensitivity check comprises releasing at least one sensitivity substance in a form of a gas from at least one sensitivity chamber in flow communication with the detector, wherein the at least one verification chamber and at least one sensitivity chamber are separate chambers, generating a sensitivity check signal using the at least one sensitivity substance, determining if the sensitivity check signal has an expected magnitude, and, based on the determining, confirming the sensitivity of the detector or determining the detector requires servicing.

10. The method of claim 9, wherein releasing the at least one sensitivity substance comprises releasing a predetermined quantity of the at least one sensitivity sub stance.

11. The method of claim 9, wherein performing the sensitivity check further comprises:
   ionizing the at least one sensitivity substance to generate the sensitivity check signal; and
   recording at least one mobility spectrum of the at least one ionized sensitivity substance, wherein the at least one mobility spectrum includes at least one peak.

* * * * *